US007384661B2

(12) United States Patent
Feather et al.

(10) Patent No.: US 7,384,661 B2
(45) Date of Patent: Jun. 10, 2008

(54) ELECTROSTATIC APPLICATION OF POWDER MATERIAL TO SOLID DOSAGE FORMS IN AN ELECTRIC FIELD

(75) Inventors: David Hoover Feather, San Diego, CA (US); Douglas Howard Nelson, Carlsbad, CA (US)

(73) Assignee: Phoqus Pharmaceuticals Limited, West Malling, Kent (GB)

( * ) Notice: Subject to any disclaimer, the term of this patent is extended or adjusted under 35 U.S.C. 154(b) by 643 days.

(21) Appl. No.: 10/451,762

(22) PCT Filed: Dec. 21, 2001

(86) PCT No.: PCT/GB01/05744

§ 371 (c)(1),
(2), (4) Date: Oct. 27, 2003

(87) PCT Pub. No.: WO02/49771

PCT Pub. Date: Jun. 27, 2002

(65) Prior Publication Data

US 2004/0052938 A1   Mar. 18, 2004

(51) Int. Cl.
*B05D 3/02* (2006.01)
*B05D 7/24* (2006.01)
*B05D 1/04* (2006.01)
(52) U.S. Cl. ............... 427/2.31; 427/485; 427/458; 427/2.1; 427/477; 427/479
(58) Field of Classification Search ............... 427/2.14, 427/458, 475, 481, 485, 471
See application file for complete search history.

(56) References Cited

U.S. PATENT DOCUMENTS 3,873,024 A    3/1975 Probst et al.

(Continued)

FOREIGN PATENT DOCUMENTS

GB    2 336 551 A    10/1999

(Continued)

OTHER PUBLICATIONS

J.F. Hughes, Electrostatic Powder Coating, 1984 Research Studies Press Ltd.England, pp. 21-23.*

(Continued)

*Primary Examiner*—William P. Fletcher, III
*Assistant Examiner*—Cachet I Sellman
(74) *Attorney, Agent, or Firm*—Buchanan Ingersoll & Rooney PC

(57) ABSTRACT

A method of electrostatically applying a powder material to a solid dosage form comprises the following steps: applying a bias voltage to generate an electric field between a source (1) of the powder material and the solid dosage form (5); applying an electrostatically charged powder material to the solid dosage form (5), the powder material being driven onto the solid dosage form (5) by the interaction of the electric field with the charged powder material, an the presence of the charged powder material on the solid dosage form serving to build up an electric charge on the solid dosage form (5) and thereby reduce the electric field generated by the bias voltage between the source (1) of powder material and the solid dosage form (5), and continuing the application of the electrostatically charged powder material to the solid dosage form (5) until the electric field between the source (1) of powder material and the solid dosage form is so small that the driving of the powder material by the electric field onto the solid dosage form (5) is substantially terminated.

39 Claims, 1 Drawing Sheet

U.S. PATENT DOCUMENTS

| | | | |
|---|---|---|---|
| 4,912,003 A | 3/1990 | Asanae et al. | |
| 5,354,583 A | 10/1994 | Zuhr et al. | |
| 5,470,603 A | 11/1995 | Staniforth et al. | |
| 5,714,007 A * | 2/1998 | Pletcher et al. | 118/629 |
| 6,045,855 A | 4/2000 | Lindqvist | |
| 6,074,688 A | 6/2000 | Pletcher et al. | |
| 6,783,768 B1 * | 8/2004 | Brown et al. | 424/443 |

FOREIGN PATENT DOCUMENTS

| | | |
|---|---|---|
| GB | 2336551 A * | 10/1999 |
| JP | 60102977 | 6/1985 |
| WO | 96/35413 | 11/1996 |
| WO | 96/35516 | 11/1996 |
| WO | 96/39257 | 12/1996 |
| WO | 98/20861 | 5/1998 |
| WO | 98/20863 | 5/1998 |
| WO | 99/51715 | 10/1999 |
| WO | 00/64592 | 11/2000 |

OTHER PUBLICATIONS

Search Report by UK Patent Office in re: UK Patent application No. 0031300.7 (now granted as UK Patent 2,370,243), Jun. 19, 2001.

Examination Report by UK Patent Office in re: UK Patent application No. 0031300.7 (now granted as UK Patent 2,370,243), Oct. 28, 2003.

International Search Report by EPO re: International patent Application PCT/GB/2001/05744, Apr. 17, 2002.

International Preliminary Examination Report by EPO re: International patent Application PCT/GB/2001/05744, Dec. 16, 2002.

Misev, Tosko Aleksandar, "Powder Coatings" chemistry and Technology; John Wiley & Sons; pp. 339-341, 1991.

Schaffert, R.M. M.A. Ph.D. "Electrophotography" The Focal Press; pp. 512-522, 1975.

Schein, L. B. "Electro-photography and Development Physics" (Revised Second Edition) Laplacian Press; pp. 139-140, 1996.

* cited by examiner

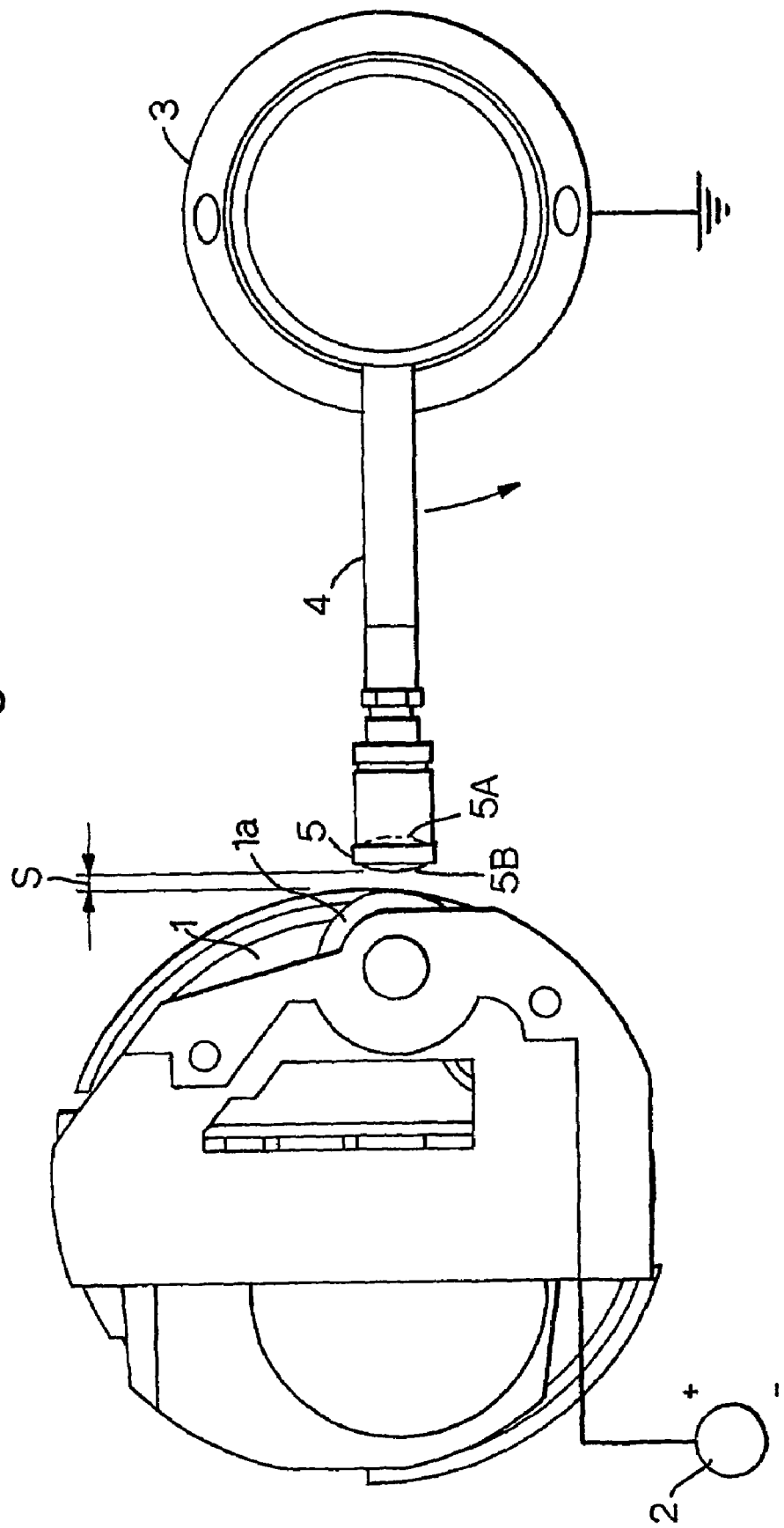

ELECTROSTATIC APPLICATION OF POWDER MATERIAL TO SOLID DOSAGE FORMS IN AN ELECTRIC FIELD

The present invention relates to a method and apparatus for the electrostatic application of powder material onto the surfaces of solid dosage forms, and more particularly, but not exclusively, pharmaceutical solid dosage forms.

A "solid dosage form" can be formed from any solid material that can be apportioned into individual units; it may be, but is not necessarily, an oral dosage form. Examples of pharmaceutical solid dosage forms include pharmaceutical tablets, pharmaceutical pessaries, pharmaceutical bougies and pharmaceutical suppositories. The term "pharmaceutical tablet" should be interpreted as covering all pharmaceutical products which are to be taken orally, including pressed tablets, pellets, capsules and spherules. Examples of non-pharmaceutical solid dosage forms include items of confectionery and washing detergent tablets.

The electrostatic application of powder material to solid dosage forms is known. In one technique, described in WO 96/35516 powder material is applied onto the solid dosage form while the solid dosage form is moving past a source of the powder material. In this case the amount of powder material applied to the solid dosage form depends upon the speed at which the solid dosage form moves past the source of powder material. In another technique, described in WO 96/39257, a predetermined amount of electrical charge is deposited onto a solid dosage form and powder material of opposite charge is brought to the solid dosage form, the amount of powder material deposited on the solid dosage form being the amount required to neutralise the charge previously deposited; in that case the amount of powder material applied to the solid dosage form is dependent upon the amount of electrical charge deposited.

An advantage of employing electrostatic techniques to deposit powder material on a solid dosage form is the potential such techniques have for providing an even distribution of powder material over the surface of the solid dosage form. Thus it is desirable that an electrostatic technique in particular should enable an even distribution of powder material to be obtained; furthermore it is desirable if the total amount of powder despatched is consistent from one dosage form to the next. In the techniques referred to above it is difficult to obtain an even distribution and a consistent total amount of powder material deposition on each solid dosage form. Small changes in charges applied to the solid dosage form and/or the physical size and positioning of the solid dosage form, are liable to have a substantial effect on the deposition of the powder material on the solid dosage form.

The present invention provides a method of electrostatically applying a powder material to a solid dosage form, the method comprising the steps of:

applying a bias voltage to generate an electric field between a source of the powder material and the solid dosage form;

applying an electrostatically charged powder material to the solid dosage form, the powder material being driven onto the solid dosage form by the interaction of the electric field with the charged powder material and the presence of the charged powder material on the solid dosage form serving to build up an electric charge on the solid dosage form and thereby reduce the electric field generated by the bias voltage between the source of powder material and the solid dosage form, and continuing the application of the electrostatically charged powder material to the solid dosage form until the electric field between the source of powder material and the solid dosage form is so small that the driving of the powder material by the electric field onto the solid dosage form is substantially terminated.

In the method of the invention, the cancellation of an electric field initially provided between the source of the powder material and the solid dosage form, as a result of a build up of charge on the solid dosage form as charged powder material is deposited thereon, causes deposition of the powder to be terminated. The initial electric field may be provided by generating a selected bias voltage, enabling the size of the field to be controlled simply and reliably. Thereafter, provided the application of the charged powder material is continued until the driving effect of the electric field is substantially terminated, and provided the charging of the powder material is maintained at a constant level, the amount of powder material transferred to the solid dosage form is largely independent of the rate at which powder material is transferred to the solid dosage form; also, there may be relative movement of the solid dosage form past the source of the powder material as the powder material is applied to the solid dosage form, in which case if the speed of movement is slow enough for the driving effect of the electric field to be terminated before the spacing of the source of powder material and the solid dosage form are so great as to cease termination, the amount of powder material transferred to the solid dosage form is largely independent of the rate at which the solid dosage form is passed over the source of powder material.

During the method of the invention the shape of the electric field between the source of powder material and the solid dosage form may change; for example, in the case of application of powder to a domed surface of a solid dosage form, a first region of the solid dosage form may receive most of the charged powder material and, as that charged powder material builds up in the first region, the electric field may be reshaped so that a second region of the solid dosage form begins to receive most of the charged powder material. For each region, deposition of powder material will continue until the electric field between the source of powder material and the solid dosage form is so small that the driving of the powder material by the electric field onto the respective region is substantially terminated. The stage at which that termination point is reached is dependent principally on the amount of charge built up on the respective region of the solid dosage form, rather than on the distance between the respective region and the source of powder material. Thus, whilst the method of the invention may be employed to apply powder material to a planar surface of a solid dosage form with all parts of the planar surface substantially equispaced from the source of powder, the method is of special advantage when employed to apply material to a domed surface, for example the domed surface of one end face of a tablet. In such a case the central region of the domed surface may be closest to the source of powder material and the electric field initially created between the source of powder material and the tablet may drive the powder material principally onto the central region; as the central region becomes coated with powder material, however, the shape of the electric field changes and more powder material is applied to a peripheral region of the domed surface surrounding the central region; thus the method may provide a substantially even coating of powder material over a domed surface of a tablet, even though outer regions of the domed surface may be further from the source of powder material than a central region.

An important variable to control when carrying out the method of the invention is the voltage that generates the electric field; in the theoretical case where there is no leakage of charge and an electric field of unchanging shape extending between parallel planes of the source of powder material at the surface of the solid dosage form to be coated, the coating will continue until a sufficient mass per unit area of charged powder material has been applied to the surface of the solid dosage form to generate a potential at that surface of the same magnitude as the voltage that generates the electric field, whereby the electric field is completely cancelled out. Also, by changing, for example, the initial bias voltage, the mass per unit area of charged powder material required to cancel out the electric field will be changed and thus the thickness of the final powder layer applied can be altered.

The electric field is preferably provided by a bias voltage that initially lies in the range of 100V to 2000V and more preferably in the range of 200V to 1200V. If the bias voltage is very low, then a relatively small electric force is applied to the powder; if the force applied to the powder is very small, it may be difficult to apply the powder uniformly. If the bias voltage is very high, it may introduce a risk of discharge of the powder by dielectric breakdown or some other mechanism.

As will be understood, for a given size of gap the electric field is proportional to the potential difference between the source of powder material and the solid dosage form and the voltages referred to above are, strictly, the potential differences; in the usual case where the solid dosage forms are at earth potential the absolute potential of the bias voltage is also the potential difference, but in a case where the solid dosage form is maintained at a potential different from earth potential, it will be appreciated that the absolute bias potential will have a value chosen to provide a potential difference that is preferably within the ranges indicated above. For a given size of air gap there will be a maximum potential difference that can be applied before there is breakdown of the air.

The electric field is preferably provided by a bias voltage that is a steady DC voltage. The polarity of the bias voltage is chosen according to whether the powder is positively or negatively charged, which in turn is dependent upon the powder and/or the charging process employed: for negatively charged powders the bias voltage is negative and for positively charged powders it is positive, the bias voltage being defined as positive when the potential at the source of powder material is greater than the potential at the solid dosage form and vice versa. Preferably an alternating voltage, which is preferably substantially higher than the DC voltage, is superimposed on the initial bias voltage. The presence of such an alternating voltage serves to mobilise the charged powder reducing any tendency of the powder particles to adhere to an adjacent surface. The alternating voltage preferably has a peak to peak value greater than, and more preferably more than twice, the peak value of the DC bias voltage. For example the alternating voltage may have a peak to peak value of the order of 5 kV. The sum of the DC bias voltage and one half of the peak to peak alternating voltage must not be so great that the potential difference causes breakdown of the air. The frequency of the alternating voltage is preferably in the range of 1 to 15 kHz. In an example of the invention described below the frequency is within that range.

The spacing between the source of powder material and the solid dosage form to which the powder material is applied is preferably in the range of 0.3 mm to 5 mm and more preferably in the range of 0.5 mm to 2.0 mm. If the spacing is relatively small by such standards then any variation from constant spacing between the solid dosage form and the source of powder material is likely to have a greater effect on the uniformity of deposition of the powder material. If the gap is increased by a small amount, one option is to keep the D.C. voltage at the same level and to increase the A.C. voltage; in that case substantially the same amount of powder material is applied before the electric field is cancelled. If the gap is increased to a greater extent, however, there will eventually be a need to increase the D.C. bias voltage. In that case a greater amount of powder will have to be applied before the field is cancelled, assuming that the amount of charge imparted to each unit mass of the powder material remains the same.

The thickness of the layer of powder material applied to the solid dosage form may be selected according to the particular requirements of a given product. Typically the thickness of the layer lies in the range of 10 to 50 μm, although in some applications a greater thickness, for example up to 200 μm may be desired; in some cases, such as where a large amount of an active powder material needs to be applied, a layer up to 1 mm thick may be built up in a series of powder application steps.

In a case where there is relative movement of the solid dosage form past the source of powder material as the powder material is applied to the solid dosage form, it is important that there is an adequate time for the dosage form to be coated with sufficient powder material to reduce the electric field to a level such that powder material is no longer driven onto the solid dosage form. Usually it will be preferable to reach that stage in a single pass of the solid dosage form past the source of powder material but it is also within the scope of the invention for the powder material to be applied in a plurality of discrete steps: for example, the powder material may be applied in a plurality of passes of the solid dosage form past the source of powder material or it may be applied by passing the solid dosage form past a plurality of sources of powder material. In the case where there are a plurality of sources of powder material, it is not necessary, especially if the same powder material is provided at each of the sources, for application of the powder material from each source to be continued until the electric field between the source and the solid dosage form is so small that the driving of the powder material onto the solid dosage form is substantially terminated; rather, that may apply for only one source, which is preferably the final source.

The aggregate time for which the application of the powder material to the solid dosage form must continue will be dependent upon the conditions under which the method is carried out, some of which have been discussed above. In a particular example of the invention described below the aggregate time required is about 400 ms. Usually the aggregate time for which the powder material is applied to a given region of the solid dosage form is in the range of 50 ms to 2 s; as will now be understood, it is possible for the solid dosage form to be exposed to the charged powder material for considerably longer without significant further deposition of powder material, but more than a small amount of such time is wasteful. Consequently it is preferred that the aggregate time for which the given region of the solid dosage form is positioned adjacent to the source of powder material is in the range of 50 ms to 2 s.

When employing a plurality of sources of powder material to increase the aggregate time for which the powder material is applied to a given region of the solid dosage form, it may be convenient to provide substantially the same electrical conditions during each application stage, but that is not essential.

In the description above referring to a plurality of sources of powder material it will generally be the case that each source comprises the same powder material. That material may be, but need not be, an active material, for example a biologically active material, that is a material which increases or decreases the rate of a process in a biological environment. The biologically active material may be one which is physiologically active.

Another possibility is to provide a plurality of sources of powder material, each comprising a respective material. In that case a plurality of superimposed layers of material may be applied. Preferably the application of electrostatically charged powder material of each given material is continued until the electric field between the source of the powder and the solid dosage form is so small that the driving of the powder by the electric field onto the solid dosage form is substantially terminated. In that way, the amount of powder in each of the layers can be controlled. Preferably the application of a further layer of powder material from a further source involves the application of a higher initial bias voltage than applied during the application of a previous layer; as an alternative to increasing the electric field in this manner, steps may be taken to discharge the powder material previously applied to the solid dosage form, after which a further layer can be applied.

From the description above, it will be seen that the invention may be employed to apply a plurality of layers of powder material to a solid dosage form, each layer consisting of a selected amount of a selected powder material. That technique is especially, but not exclusively, useful in the production of what is commonly referred to as a controlled release or modified release solid dosage form. In such a case one, some or all of the layers may include active material. Thus dosage forms having two or more layers of different active material, with or without other intervening layers, may be employed.

Preferably the step of providing the electric field between the source of powder material and the solid dosage form comprises the step of providing respective electrically conducting members at the powder source and at the solid dosage form, and applying a potential difference between the electrically conducting members. Preferably the electrically conducting member at the powder source comprises an electrically conducting roller.

The powder material may be electrostatically charged in any suitable way. For example, it may be charged triboelectrically.

The solid dosage form may be a domed tablet having a pair of opposite domed end faces joined by a cylindrical side wall. In such a case, the electrostatically charged powder material may be applied uniformly over the whole of one domed end face of the tablet. The solid dosage form may, more particularly, be an oral dosage form and/or a pharmaceutical dosage form, for example a pharmaceutical tablet.

Preferably, the method further comprises the step of treating the powder material to fix it on the solid dosage form. The treatment of the powder material to fix it to the solid dosage form preferably involves a heating step, preferably using convection, but other forms of heating such as infra red radiation or conduction or induction may be used. The powder material should be heated to a temperature above its softening point, and then allowed to cool to a temperature below its glass transition temperature (Tg). It is important to control the amount of heat applied to avoid degradation of the powder material and/or the solid dosage form. The amount of heat required may be reduced by applying pressure to the powder material. Alternatively, the powder material may include a polymer which is cured during the treatment, for example, by irradiation with energy in the gamma, ultra violet or radio frequency bands.

The method may comprise the step of applying powder material to a first surface of the solid dosage form, and the subsequent step of applying powder material to a second surface of the solid dosage form. Where the method is being used to apply a continuous coating to a solid dosage form, such a step will usually be necessary if the whole surface of the dosage form is to be coated.

Preferably, the method is carried out as a continuous process.

The method of the present invention is not restricted to the use of any particular type of powder material. The powder materials described in WO 96/35413 are examples of suitable powder materials.

The powder material may include a biologically active material, that is, a material which increases or decreases the rate of a process in a biological environment. The biologically active material may be one which is physiologically active.

Conventionally, where an active material is to be administered in solid dosage form, the active material is mixed with a large volume of non-active "filler" material in order to produce a dosage form of manageable size. It has been found, however, that it is difficult to control accurately the amount of active material contained in each dosage form, leading to poor dose uniformity. That is especially the case where the required amount of active material in each dosage form is very low.

By electrostatically applying active material to a dosage form, it has been found to be possible to apply accurately very small amounts of active material to the dosage form, leading to improved dose reproducibility.

The powder material comprising active material may be applied to a solid dosage form containing the same or a different active material, or may be applied to a solid dosage form containing no active material.

The present invention also provides an apparatus for electrostatically applying a powder material to a solid dosage form, the apparatus being arranged to carry out the method defined above and comprising a source of charged powder material, a support for supporting a solid dosage form in the vicinity of the source of powder material, a voltage source for generating an electric field between the source of powder material and a solid dosage form, the apparatus being arranged such that electrostatically charged powder material is, in use, applied to the solid dosage form, the powder material being driven onto the solid dosage form by the interaction of the electric field with the charged powder material, the presence of the charged powder material on the solid dosage form serving to build up an electric charge on the solid dosage form and thereby reduce the electric field between the source of powder material and the solid dosage form, and the application of the electrostatically charged powder material to the solid dosage form is continued until the electric field between the source of powder material and the solid dosage form is so small that the driving of the powder material by the electric field onto the solid dosage form is substantially terminated.

The apparatus may be such that it is suitable for carrying out any of the methods referred to above.

By way of example, embodiments of the invention will now be described with reference to the accompanying drawings, of which:

FIG. 1 is a schematic side view of an apparatus for experimental use in the electrostatic application of powder material onto an end face of a tablet.

FIG. 1 is a schematic drawing of an apparatus that we have used to implement the invention on a laboratory scale.

The apparatus generally comprises a source 1 of electrostatically charged powder material, connected to a variable voltage source 2, and a rotatable hub 3 from which an arm 4 projects radially, with a tablet 5 being carried on the free end of the arm 4. Powder material in the source 1 is fed to a roller 1a and is charged triboelectrically during its passage to the roller 1a. The roller 1a is electrically conducting and is connected to the voltage source 2. The hub 3 is electrically earthed and the arm 4 provides an electrical connection between a rear face 5A of the tablet 5 and earth.

In use the hub 3 is rotated at a constant speed by an electric motor (not shown) causing the tablet 5 to pass through a region adjacent to the source 1 of powder material once for each revolution of the hub 3. When the tablet 5 is closest to the powder material source 1, there is a spacing 'S' between the source 1 and a front face 5B of the tablet.

The apparatus has been used to carry out a variety of powder application processes, Examples of which will be given below.

In the Examples, the spacing 'S' between the source 1 and the front face 5B of the tablet was 1 mm; the hub 3 was rotated at a constant speed of 0.9 r.p.m. resulting in a speed of movement of the tablet 5 past the powder material source 1 of 4.8 mm/s leading to an effective "dwell time" of the tablet face adjacent to the source 1 of 400 mS.

The tablet 5 onto which powder material was supplied was of conventional shape having two domed end faces joined by a cylindrical side wall; the cylindrical side wall was of diameter 10 mm and of height 2 mm; the separation of the domed end faces at their centres, where the separation was greatest, was 3.8 mm. The tablet was a solid aluminium tablet of 6061-T6 aluminium.

The powder material provided at the source 1 was a material used as a toner in electrostatic photocopying, namely that known as Optra C and sold by Lexmark. The particles of toner were generally of about 10 μm diameter.

EXAMPLE 1

The voltage source 2 was set to provide a DC bias voltage initially of 500V with an AC voltage of 5000V peak to peak at 2 kHz superimposed on the DC voltage. A tablet was mounted on the free end of the arm 4 and rotated by the hub 3 as described above at a speed of about 4.8 mm/s. It was observed that during the first few passes the powder material at the source 1 was driven from the source onto the face 5B of the tablet 5 each time the tablet passed the source. The charge on the powder at the powder source was measured as approximately 7.2 μC/g, having been generated by triboelectric charging. In the example described both the charge on the powder and the voltage bias at the powder source were negative. The mass of powder on the tablet was measured after each pass and it was found that initially there was an approximately linear relationship between the number of passes of the tablet past the source and the amount of powder material applied to the tablet. Then the additional amount of powder applied during one further pass began to reduce and after 4 passes no further application of powder onto the tablet was detected. The total mass of powder material applied to the tablet at the end of the procedure was about 3.2 mg provided by a layer of material of about 4.1 mg/cm². After 4 passes, when no further application of powder was detected, the voltage of the powder on the solid dosage form was renewed and found to be −490V.

EXAMPLE 2

The same procedure was carried out as in Example 1 but in this case the initial DC bias voltage was 750V, with the AC voltage remaining at 5000V peak to peak at 2 kHz. With the higher initial bias voltage, the rate of transfer of powder material was faster; after 5 passes, no further application of powder onto the tablet was detected. The total mass of powder material applied to the tablet at the end of the procedure was about 3.8 mg, provided by a layer of material of about 4.9 mg/cm². The final voltage of the powder on the solid dosage form was measured and found to be −733V.

EXAMPLES 3 AND 4

The same procedure as in Examples 1 and 2 was carried out, with further settings of the voltage source. The results of that, as well as the results from Examples 1 and 2 are tabulated below.

|  | DC Voltage V | AC Voltage at 2 kHz (peak to peak) V | No. of passes before no increase in material deposit | Final mass of material transferred mg | Final voltage of material deposit |
|---|---|---|---|---|---|
| Example 1 | −500 | 5000 | 4 | 3.2 | −490 |
| Example 2 | −750 | 5000 | 5 | 3.8 | −733 |
| Example 3 | −1000 | 5000 | 5 | 4.3 | −971 |
| Example 4 | −250 | 5000 | 3 | 2.0 | −243 |

A mass of 1 mg of material transferred onto a tablet corresponds to a thickness of about 11.6 microns of the material on the tablet. Thus in the examples above the amounts of material transferred corresponds to thicknesses on the tablet in the range of 23 to 50 microns.

When applying the invention on a commercial scale, the powder supply arrangement can still conveniently be as shown in FIG. 1. It is, however, preferable that the arrangement for conveying tablet cores past the powder supply arrangement is able to convey a plurality of tablets, rather than just a single tablet as in the case of the apparatus shown in FIG. 1. Such conveying apparatus does not form part of the present invention and will not be described in detail in this specification. Examples of conveying arrangements that may be employed are shown in WO 96/35516, WO 98/20861 and WO 98/20863, the contents of which are incorporated herein by reference. In the apparatus described in those documents, there is in each case one or more powder supply sources; for example, FIG. 2 of WO 98/20861 shows a powder supply source 16; as will be understood, the powder supply source 16 of WO 98/20861 may be replaced by the source 1 of FIG. 1 of the present invention to provide one example of a commercial apparatus embodying the invention. Also WO 96/34513, the contents of which are incorporated herein by reference, gives details of materials that may be employed in embodiments of the present invention.

The invention is claimed:

1. A method of electrostatically applying a powder material to a solid dosage form, the method comprising:
    applying a bias voltage to generate an electric field between a source of the powder material and the solid dosage form;
    applying an electrostatically charged powder material to the solid dosage form, the powder material being driven onto the solid dosage form by the interaction of the electric field with the charged powder material, and the presence of the charged powder material on the solid dosage form serving to build up an electric charge on the solid dosage form and thereby reduce the electric field generated by the bias voltage between the source of powder material and the solid dosage form, and
    continuing the application of the electrostatically charged powder material to the solid dosage form until the electric field between the source of powder material and the solid dosage form is so small that the driving of the powder material by the electric field onto the solid dosage form is substantially terminated.

2. A method according to claim 1, in which the electric field is provided by a bias voltage that initially lies in the range of 100V to 2000V.

3. A method according to claim 2, in which the bias voltage initially lies in the range of 200V to 1200V.

4. A method according to claim 1 or 2, in which the spacing between the source of powder material and the solid dosage form to which the powder material is applied is in the range of 0.3 mm to 5 mm.

5. A method according to claim 4, in which the spacing between the source of powder material and the solid dosage form to which the powder material is applied is in the range of 0.5 mm to 2.0 mm.

6. A method according to claim 1, in which the electric field is provided by a bias voltage that is a steady DC voltage.

7. A method according to claim 6, in which an alternating voltage is superimposed on the bias voltage.

8. A method according to claim 7, in which the alternating voltage has a peak to peak value greater than the peak value of the DC bias voltage.

9. A method according to claim 8, in which the alternating voltage has a peak to peak value that is more than twice the peak value of the DC bias voltage.

10. A method according to claim 1, in which the thickness of the layer of powder material applied to the solid dosage form lies in the range of 10 to 50 μm.

11. A method according to claim 1, in which there is relative movement of the solid dosage form past the source of powder material as the powder material is applied to the solid dosage form.

12. A method according to claim 11, in which the powder material is applied in a single pass of the solid dosage form past the source of powder material.

13. A method according to claim 11, in which the powder material is applied in a plurality of passes of the solid dosage form past the source of powder material.

14. A method according to claim 11, in which the powder material is applied by passing the solid dosage form over a plurality of sources of powder material.

15. A method according to claim 1, in which the aggregate time for which the powder material is applied to a given region of the solid dosage form is in the range of 50 ms to 500 ms.

16. A method according to claim 1, in which the aggregate time for which a given region of the solid dosage form is positioned adjacent to the source of powder material is in the range of 50 ms to 2 s.

17. A method according to claim 1, in which a plurality of sources of powder material are provided, each comprising a respective material.

18. A method according to claim 17, in which the application of each electrostatically charged powder material is continued until the respective electric field between each of the sources of the powder material and the solid dosage form is so small that the driving A method according to claim 17, in which the application of each electrostatically charged powder material is continued until the electric field between the source of the powder material and the solid dosage form is so small that the driving of the powder by the electric field onto the solid dosage form is substantially terminated.

19. A method according to claim 17 or 18, in which the application of a further layer of powder material from a further source involves the application of a higher initial bias voltage than applied during the application of a previous layer.

20. A method according to claim 1 in which the step of providing the electric field between the source of powder material and the solid dosage form comprises providing respective electrically conducting members at the powder source and at the solid dosage form, and applying a potential difference between the electrically conducting members.

21. A method according to claim 1, in which the solid dosage form is a domed tablet having a pair of opposite domed end faces joined by a cylindrical side wall.

22. A method according to claim 21, in which the electrostatically charged powder material is applied uniformly over the whole of a domed end face of the tablet.

23. A method according to claim 1, in which the solid dosage form is an oral dosage form.

24. A method according to claim 1, in which the solid dosage form is a pharmaceutical dosage form.

25. A method according to claim 24, in which the pharmaceutical dosage form is a pharmaceutical tablet.

26. A method according to claim 1 further comprising treating the powder material to fix it on the solid dosage form.

27. A method according to claim 26, in which the treatment of the powder material to fix it on the solid dosage form includes a heating step.

28. A method according to claim 1 comprising applying the powder material to a first surface of the solid dosage form and subsequently applying the powder material to a second surface of the solid dosage form.

29. A method according to claim 1, in which the powder material includes a biologically active material.

30. A method according to claim 7, in which the electric field is provided by a bias voltage that initially lies in the range of 100V to 2000V.

31. A method according to claim 7, in which the spacing between the source of powder material and the solid dosage form to which the powder material is applied is in the range of 0.3 mm to 5 mm.

32. A method according to claim 11, in which the spacing between the source of powder material and the solid dosage form to which the powder material is applied is in the range of 0.3 mm to 5 mm.

33. A method according to claim 11, in which an alternating voltage is superimposed on the bias voltage.

34. A method according to claim 12, in which the spacing between the source of powder material and the solid dosage form to which the powder material is applied is in the range of 0.3 mm to 5 mm.

35. A method according to claim 12, in which an alternating voltage is superimposed on the bias voltage.

36. A method according to claim 21, in which the spacing between the source of powder material and the solid dosage form to which the powder material is applied is in the range of 0.3 mm to 5 mm.

37. A method according to claim 21, in which an alternating voltage is superimposed on the bias voltage.

38. A method according to claim 21, in which there is relative movement of the solid dosage form past the source of powder material as the powder material is applied to the solid dosage form.

39. A method according to claim 38, in which the powder material is applied in a single pass of the solid dosage form past the source of powder material.

* * * * *